(12) United States Patent
Harty et al.

(10) Patent No.: US 10,517,275 B2
(45) Date of Patent: Dec. 31, 2019

(54) METHOD, A DEVICE AND A SYSTEM FOR DETERMINING A STATE OF AN ANIMAL

(71) Applicant: DAIRYMASTER, Causeway (IE)

(72) Inventors: Edmond Patrick Harty, Ballyheigue (IE); Liam Eoghan Mullane, Newcastlewest (IL); John Gerard Daly, Tralee (IE); Christopher Kinsella, Listowel (IE)

(73) Assignee: DAIRYMASTER, County Kerry (IE)

( * ) Notice: Subject to any disclaimer, the term of this patent is extended or adjusted under 35 U.S.C. 154(b) by 421 days.

(21) Appl. No.: 14/897,483

(22) PCT Filed: Jun. 16, 2014

(86) PCT No.: PCT/IE2014/000010
§ 371 (c)(1),
(2) Date: Dec. 10, 2015

(87) PCT Pub. No.: WO2014/199362
PCT Pub. Date: Dec. 18, 2014

(65) Prior Publication Data
US 2016/0135433 A1    May 19, 2016

(30) Foreign Application Priority Data

Jun. 14, 2013  (IE) .................................. S2013/0193
Jun. 14, 2013  (IE) .................................. S2013/0194

(51) Int. Cl.
*A01K 29/00* (2006.01)
*A01K 11/00* (2006.01)
(Continued)

(52) U.S. Cl.
CPC .......... *A01K 29/005* (2013.01); *A01K 11/006* (2013.01); *A61B 5/0022* (2013.01);
(Continued)

(58) Field of Classification Search
CPC .. A01K 29/005; A01K 11/006; A61B 5/0022; A61B 5/1114; A61B 5/1118;
(Continued)

(56) References Cited

U.S. PATENT DOCUMENTS

2004/0097814 A1* 5/2004 Navakatikyan ........ A61B 5/024
600/485
2006/0155172 A1* 7/2006 Rugg ................... A61B 5/1123
600/300
(Continued)

FOREIGN PATENT DOCUMENTS

JP    2003-219757 A    8/2003
WO    2007/132245 A1    11/2007
(Continued)

OTHER PUBLICATIONS

Written Opinion of the International Searching Authority of PCT/IE2014/000010 dated Sep. 2, 2014.
(Continued)

*Primary Examiner* — Daniel L Cerioni
(74) *Attorney, Agent, or Firm* — Sughrue Mion, PLLC

(57) ABSTRACT

A device (5) attached to the neck (6) of an animal (2) comprises an accelerometer (17) which produces first and second signals indicative of the raised and lowered state of the head (7) of the animal (2) and movement of the animal (2). A microprocessor (20) in the device (5) processes the first and second signals to determine if the animal is ruminating, resting, feeding or in a highly active state during respective second predefined time periods of approximately 15 minutes duration. Data indicative of the ruminating, resting, feeding and the highly active state of the animal is stored by the microprocessor (20) in the device (5) and is (Continued)

Figure 1:
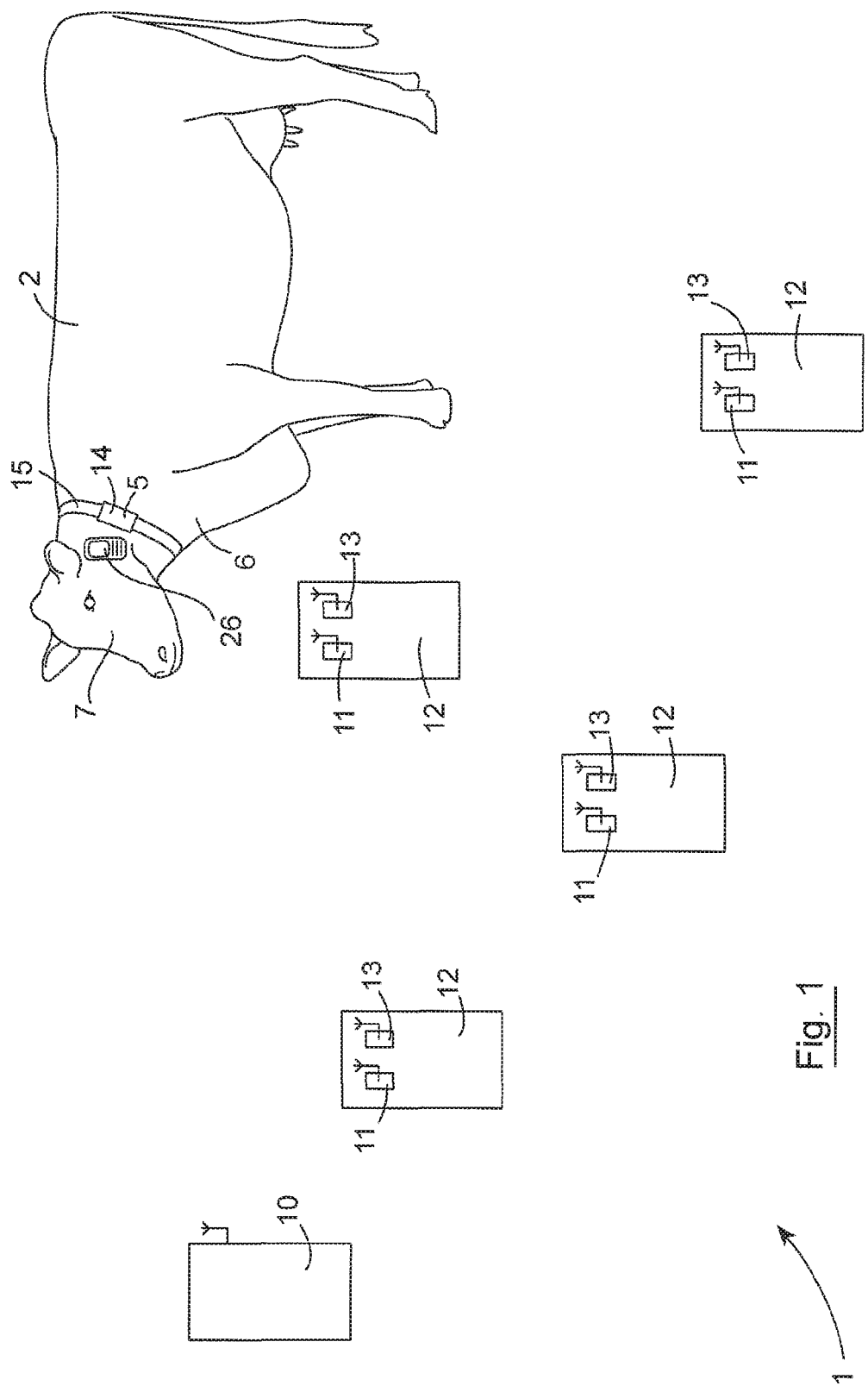

periodically wirelessly communicated to a base station computer which further processes the data to determine various health states of the animal.

19 Claims, 4 Drawing Sheets

(51) Int. Cl.
  *A61B 5/00* (2006.01)
  *A61B 5/11* (2006.01)
(52) U.S. Cl.
  CPC ........... *A61B 5/1114* (2013.01); *A61B 5/1118* (2013.01); *A61B 5/1121* (2013.01); *A61B 5/1123* (2013.01); *A61B 5/7246* (2013.01); *A61B 5/7278* (2013.01); *A61B 5/7282* (2013.01); *A61B 2503/40* (2013.01); *A61B 2562/0219* (2013.01)
(58) Field of Classification Search
  CPC ... A61B 5/1121; A61B 5/1123; A61B 5/7246; A61B 5/7278; A61B 5/72872
  USPC ........................................................ 600/595
  See application file for complete search history.

(56) References Cited

U.S. PATENT DOCUMENTS

| | | | |
|---|---|---|---|
| 2007/0130893 A1* | 6/2007 | Davies | A01K 11/008 54/1 |
| 2008/0021352 A1* | 1/2008 | Keegan | A61B 5/0002 600/595 |
| 2009/0037056 A1* | 2/2009 | Erb | B60R 21/0132 701/46 |
| 2012/0186091 A1* | 7/2012 | Yao | G01C 17/30 33/355 R |
| 2012/0274442 A1* | 11/2012 | Mottram | A01K 29/005 340/5.8 |
| 2013/0316753 A1* | 11/2013 | Van Dijk | A01K 11/006 455/517 |
| 2014/0275824 A1* | 9/2014 | Couse | A01K 29/005 600/301 |
| 2014/0347262 A1* | 11/2014 | Paek | G09G 3/20 345/156 |
| 2015/0351885 A1* | 12/2015 | Kool | A61D 17/002 600/551 |

FOREIGN PATENT DOCUMENTS

| | | |
|---|---|---|
| WO | 2011/069512 A1 | 6/2011 |
| WO | 2013/005038 A1 | 1/2013 |

OTHER PUBLICATIONS

International Search Report of PCT/IE2014/000010 dated Sep. 2, 2014.

European Search Report dated Sep. 27, 2018 in EP 14 736 032.5.

* cited by examiner

METHOD, A DEVICE AND A SYSTEM FOR DETERMINING A STATE OF AN ANIMAL

CROSS REFERENCE TO RELATED APPLICATIONS

This is a National Stage of International Application No. PCT/IE2014/000010 filed Jun. 16, 2014, claiming priority based on Irish Patent Application No. S2013/0193 filed Jun. 14, 2013 and Irish Patent Application No. S2013/0194 filed Jun. 14, 2013, the contents of all of which are incorporated herein by reference in their entirety.

The present invention relates to a method, a device and a system for determining the state of an animal.

Devices and methods for determining the state of an animal are known. Such devices, typically, are electronic devices and they may include sensors, for monitoring, for example, the temperature, heart rate, blood pressure and the like of an animal. Other such devices are provided for determining when an animal is in a relatively highly active state in order to facilitate the detection of oestrus in the animal. Attempts have been made to provide methods and devices for determining other states of an animal, for example, for determining when an animal is feeding or ruminating. However, to date such methods and devices lack accuracy.

There is therefore a need for a method for determining at least one state of an animal, for example, ruminating, resting, feeding or the like, which addresses lack of accuracy issues of known methods and devices. There is also a need for a device and a system for determining at least one of such states of an animal which addresses accuracy issues of known methods and devices.

The present invention is directed towards providing such a method, a device and a system.

According to the invention there is provided a method for determining a state of an animal, the method comprising reading signals from a sensing means indicative of two sensed conditions of the animal, determining at least one state of the animal from a plurality of states in response to the frequency of the read signal being indicative of one of the sensed conditions being in a predefined state.

In one aspect of the invention a first one of the sensed conditions of the animal comprises the orientation of the head of the animal.

In another aspect of the invention a second one of the sensed conditions of the animal comprises the level of activity of the animal.

Preferably, at least one of the determined states of the animal comprises ruminating.

In one aspect of the invention the animal is determined as ruminating in response to the read signals indicative of the first one of the sensed conditions being indicative of the head of the animal being in a raised state, and the frequency of the read signal being indicative of ruminating.

In another aspect of the invention the frequency of the read signal is determined as being indicative of ruminating in response to one or more frequency components of the frequency of the read signal lying within a predefined frequency range indicative of the frequency of ruminating. Preferably, the frequency of the read signal is determined as being indicative of ruminating in response to the magnitude of the frequency component of the read signal which lies within the predefined frequency range being of magnitude lying within a predefined range of magnitudes indicative of ruminating.

In one embodiment of the invention where two or more frequency components of the read signal lie within the predefined frequency range indicative of ruminating, the average value of the magnitudes of the two or more frequency components which lie within the predefined frequency range is computed, and the frequency of the read signal is determined as being indicative of ruminating in response to the average value of the magnitudes of the two or more frequency components of the read signal which lie within the frequency range indicative of ruminating being within the predefined range of magnitudes indicative of ruminating.

In another aspect of the invention one of the determined states of the animal is feeding.

In another aspect of the invention the state of the animal is determined as feeding in response to the read signal indicative of the first one of the sensed conditions being indicative of the head of the animal being in a lowered state, and the second one of the sensed conditions indicative of the level of activity of the animal being indicative of a low level of activity indicative of feeding.

Preferably, the read signal indicative of the second one of the sensed conditions is determined as being indicative of a low level of activity of the animal which is indicative of feeding in response to the spread of values of the magnitude of the read signals indicative of the second one of the sensed conditions lying within a first predefined range of magnitude values indicative of feeding.

In another aspect of the invention the read signal indicative of the second one of the sensed conditions is determined as being indicative of a low level of activity which is indicative of feeding in response to the spread of the values of the magnitude of the read signal indicative of the second one of the sensed conditions about the mean value thereof lying within a range indicative of the first predefined range of magnitude values.

In another aspect of the invention one of the determined states of the animal comprises resting.

In another aspect of the invention the state of the animal is determined as resting in response to the read signal indicative of the second one of the sensed conditions being indicative of a low level of activity of the animal indicative of resting.

In another aspect of the invention the read signals indicative of the second one of the sensed conditions is determined as being indicative of a low level of activity which is indicative of resting in response to the spread of values of the magnitude of the read signal indicative of the second one of the sensed conditions lying within a second predefined range of magnitude values indicative of resting.

Preferably, the read signals indicative of the second one of the sensed conditions is determined as being indicative of a low level of activity of the animal which is indicative of resting in response to the spread of the values of the magnitude of the read signal indicative of the second one of the sensed conditions about the mean value thereof lying within a range indicative of the second predefined range of magnitude values.

In a further aspect of the invention the second predefined range of magnitude values of the spread of values of the magnitude of the read signal indicative of the second one of the sensed conditions is less than the first predefined range of magnitude values of the spread of values of the magnitude of the read signal indicative of the second one of the sensed conditions.

In another aspect of the invention the state of the animal is determined as ruminating in response to the spread of values of the magnitude of the read signal indicative of the second one of the sensed conditions lying within a third predefined range of magnitude values indicative of ruminating.

Preferably, the state of the animal is determined as ruminating in response to the spread of the values of the magnitude of the read signal indicative of the second one of the sensed conditions about the mean value thereof lying within a range of magnitude values indicative of the third predefined range of magnitude values.

In another aspect of the invention the third predefined range of magnitude values lies between the first predefined range of magnitude values and the second predefined range of the three values.

In a further embodiment of the invention the state of the animal is determined as being in a highly active state in response to the read signals indicative of the first one of the sensed conditions being indicative of the head of the animal being in a raised state, and the second one of the sensed conditions being indicative of a high level of activity of the animal.

In another aspect of the invention the state of the animal is determined as being in a highly active state in response to the spread of values of the magnitude of the read signal indicative of the second one of the sensed conditions lying within a fourth predefined range of magnitude values indicative of the highly active state.

Preferably, the animal is determined as being in the highly active state in response to the spread of the values of the magnitude of the read signal indicative of the second one of the sensed conditions about the mean value thereof lying within a range indicative of the fourth predefined range of magnitude values.

In another aspect of the invention the fourth predefined range of magnitude values is greater than the first predefined range of magnitude values.

In one embodiment of the invention the state of the head of the animal and the spread of the values of the magnitude of the read signal indicative of the second one of the sensed conditions are initially determined. Preferably, the animal is determined as being in a resting state if the spread of the values of the magnitude of the read signal indicative of the second one of the sensed conditions lies within the second predefined range of magnitude values.

Preferably, the animal is determined as feeding in response to the spread of the values of the magnitude of the read signal indicative of the second one of the sensed conditions lying within the first predefined range of magnitude values, and the head of the animal being determined as being in the lowered state.

Advantageously, the frequency of the read signal is analysed in order to determine if the animal is ruminating in response to the head of the animal being determined as being in the raised state, and the spread of values of the magnitude of the read signal indicative of the second one of the sensed conditions lying within the third predefined range of magnitude values.

In one embodiment of the invention the frequency of the read signal is determined from the frequency domain of the read signal.

Preferably, a Fast Fourier Transform is carried out on the read signal indicative of the second one of the sensed conditions to produce a frequency response of the read signal indicative of the second one of the sensed conditions, so that the frequency domain of the read signal indicative of the second one of the sensed conditions can be analysed.

In one embodiment of the invention the signal is read from the sensing means during respective first predefined time periods, and the state of the animal during each corresponding first predefined time period is determined from the read signal at the end of the first predefined time period and is stored.

Preferably, the states of the animal determined at the respective ends of a plurality of sequential ones of the first predefined time periods during respective second predefined time periods are tabulated at the ends of the respective corresponding second predefined time periods, and the states of the animal and the number of the first predefined time periods in each second predefined time period in which the animal was in the respective states are stored, each second predefined time period being of duration to comprise a predefined number of the first predefined time periods.

Preferably, the first time periods run consecutively one after the other.

In one embodiment of the invention each first predefined time period is of duration in the range of 5 seconds to 25 seconds, and preferably, each first predefined time period is of duration in the range of 10 seconds to 12 seconds, and ideally, each first predefined time period is of duration of approximately 10 seconds, and preferably, 10.24 seconds.

In another embodiment of the invention each second predefined time period is of duration up to 60 minutes, and preferably, each second predefined time period is of duration up to 30 minutes, and advantageously, each second predefined time period is of duration of approximately 15 minutes.

Advantageously, the second predefined time periods run consecutively one after the other.

In another embodiment of the invention the signals read from the sensing means are sampled at a rate in the range of 6 Hz to 50 Hz, and preferably, at a sampling rate in the range of 6 Hz to 25 Hz, and advantageously, at a sampling rate of approximately 12.5 Hz.

Advantageously, the sampled values of the signal read from the sensing means are buffered during each first predefined time period.

In another embodiment of the invention the sensing means comprises at least one sensor, and preferably, the sensing means comprises an accelerometer. Advantageously, the accelerometer is configured to produce a signal indicative of the acceleration to which the accelerometer is subjected along at least one axis thereof. Preferably, the accelerometer is adapted for attaching to the animal, and is configured for determining the state of the head of the animal. Advantageously, the signal indicative of the acceleration to which the accelerometer is subjected along the axis thereof is indicative of the state of the head of the animal.

In another embodiment of the invention the signal read from the accelerometer indicative of the acceleration to which the accelerometer is subjected along the axis thereof is indicative of the level of activity of the animal.

In another aspect of the invention the accelerometer produces signals indicative of acceleration to which the accelerometer is subjected along two axes perpendicular to each other, and preferably, the accelerometer is configured for attaching to the animal so that the signal produced by the accelerometer indicative of the acceleration to which the accelerometer is subjected along one of the axes thereof is indicative of the state of the head of the animal, and the signal indicative of the acceleration to which the accelerometer is subjected along the other one of the axes is indicative of the level of activity of the animal.

Advantageously, the signals read from the sensing means are processed in a microprocessor.

In one aspect of the invention data in which data relating to the state of the animal is communicated to a remote communicating means.

Advantageously, the remote computing means comprises one of a computer located at a remote base station and a cloud computer server.

In another aspect of the invention the data relating to the state of the animal is communicated to the remote computing means via a relay station.

Advantageously, the data relating to the state of the animal is communicated in response to the animal being in the vicinity of the relay station.

In a further aspect of the invention the data relating to the state of the animal is transmitted wirelessly to the remote computing means.

In a further aspect of the invention the data relating to the state of the animal is communicated to a portable handheld powered device in a Near Field Communications protocol.

In a further embodiment of the invention the data relating to the state of the animal is further processed in one or more of the remote computing means and the portable handheld powered device to determine further states of the animal, including the onset of oestrus, and other health states of the animal.

In another embodiment of the invention data indicative of at least one predefined location visited by the animal is stored, and preferably, the time at which the animal visited the at least one predefined location is stored, and ideally, the duration of the visit to the at least one predefined location is stored. Preferably, the identity of the at least one predefined location is determined from an identification signal received when the animal is adjacent the at least one predefined location, and preferably, the identification signal is received wirelessly.

In one embodiment of the invention the identification signal is generated adjacent the at least one predefined location, and in an alternative embodiment of the invention the identification signal is derived from a means adjacent the at least one predefined location capable of producing or configuring a signal to be indicative of the at least one predefined location. In one embodiment of the invention the means for producing or configuring the signal to be indicative of the at least one predefined location comprises a means for wirelessly transmitting a signal indicative of the at least one predefined location.

Preferably, data indicative of a plurality of respective predefined locations visited by the animal is stored, and advantageously, the respective times and the respective durations of the visits to the respective ones of the predefined locations are stored.

Advantageously, the data indicative of the predefined locations, and preferably the times at which the predefined locations are visited, and advantageously, the durations of the visits to the predefined locations are communicated to remote computing means. Advantageously, the data indicative of the locations visited by the animal, the times at which the predefined locations are visited and the durations of the visits to the respective predefined locations are stored for each second predefined time period, and advantageously is communicated along with the data stored relating to the states of the animal for each of the second predefined time periods.

The invention also provides a device for determining the state of an animal, the device comprising a sensing means for monitoring at least two conditions of the animal and for producing signals indicative of the sensed conditions, and a signal processor configured to read the signals from the sensing means, and to carry out the method according to the invention for determining the state of the animal.

Preferably, the signal processor is configured to determine at least one state of the animal from a plurality of states in response to the frequency of the read signal being indicative of one of the sensed conditions being in a predefined state.

In one aspect of the invention the device comprises a communicating means for communicating data relating to the state of the animal to a remote computing means, and preferably, for communicating the data relating to the state of the animal wirelessly. Advantageously, the communicating means comprises a radio transceiver, which preferably, is operable in a high powered mode for long range communications and in a low powered mode for short range communications. Advantageously, the communicating means comprises a short range receiver for wirelessly receiving a wirelessly transmitted signal at a short range, which advantageously, comprises a short range receiver.

In one embodiment of the invention the short range receiver is adapted for receiving an inductively coupled low frequency signal.

Preferably, the signal processor is configured to read identification signals received from respective ones of the predefined locations as the animal visits each of the predefined locations, and advantageously, the signal processor is configured to store the identities of the respective predefined locations, the times at which the respective predefined locations are visited by the animal, and the durations of the respective visits by the animal to each of the respective predefined locations.

In one embodiment of the invention the communicating means is adapted to receive the identification signals from each of the predefined locations, and preferably, the signal processor is adapted to read the identification signals received by the communicating means in response to reception thereof. Preferably, the identification signals from the predefined locations are received through the receiver.

In another embodiment of the invention the device is configured to store an identifying code identifying the identity of the device.

Advantageously, the communicating means comprises a low energy communications module. Preferably, the low energy communications module is configured to facilitate reading out the identifying code from the device, and preferably, the low energy communications module is configured to facilitate reading out the identifying code through an external powered device, such as a smart mobile phone configured by a suitable software application, namely, an app, to permit reading of the identifying code from the device through the low energy communications module.

Advantageously, the low energy communications module is configured to permit two-way communications between the signal processor of the device and the external powered device. Advantageously, the low energy communications module is configured to facilitate programming of the signal processor of the device by the external powered device, and advantageously, the low energy communications module is configured to permit reprogramming of the signal processor of the device by the external powered device.

In another embodiment of the invention the low energy communications module is configured to permit one or both of uploading and downloading of data to and from the device by the external powered device.

In one aspect of the invention the low energy communications module comprises a Near Field Communications module. In an alternative aspect of the invention the lower energy communications module comprises a blue tooth low energy module.

In one embodiment of the invention the transceiver is configured to transmit data stored in the device which is indicative of the states of the animal and the predefined locations visited by the animal, the times and durations of the respective visits, and preferably, the data is wirelessly transmitted by the transceiver.

In one aspect of the invention the transceiver is responsive to an activation signal received from the remote computing means to transmit the stored data relating to the states of the animal and the predefined locations visited by the animal, the times and the durations of the respective visits.

In another embodiment of the invention the data indicative of the states of the animal and the identity of the predefined locations visited by the animal, the times and durations of the visits are transmitted through the transceiver at predefined time intervals.

In a further embodiment of the invention the transceiver is responsive to an activation signal received from one of a plurality of relay stations to transmit the stored data relating to the states of the animal and the predefined locations visited by the animal, the times and durations of the respective visits for reception by the relay station, for subsequent transmission by the relay station to the remote computing means.

Advantageously, the transceiver is operable in two power modes, namely, a high power mode for transmitting data to the base station, and a low power mode for transmitting the data to the relay station.

In one aspect of the invention the sensing means comprises an accelerometer.

Preferably, the accelerometer is configured to produce a signal indicative of the acceleration to which the accelerometer is subjected along at least one axis thereof.

Advantageously, the accelerometer is adapted for attaching to the animal, and is configured for determining the state of the head of the animal.

In another aspect of the invention the signal indicative of the acceleration to which the accelerometer is subjected along the axis thereof is indicative of the state of the head of the animal.

Preferably, the signal read from the accelerometer indicative of the acceleration to which the accelerometer is subjected along the axis thereof is indicative of the level of activity of the animal.

In a further aspect of the invention the accelerometer produces signals indicative of acceleration to which the accelerometer is subjected along two axes perpendicular to each other.

Preferably, the accelerometer is configured for attaching to the animal so that the signal produced by the accelerometer indicative of the acceleration to which the accelerometer is subjected along one of the axes thereof is indicative of the state of the head of the animal, and the signal indicative of the acceleration to which the accelerometer is subjected along the other one of the axes is indicative of the level of activity of the animal.

The invention also provides a system for determining a state of an animal, the system comprising a device according to the invention for determining the state of an animal, and a remote computing means for receiving data communicated wirelessly by the device.

Preferably, at least one relay station is provided for receiving the data transmitted by the device and for relaying the received data to the remote computing means. Advantageously, each relay station comprises a transmitter for transmitting an activation signal to the device to activate the device to transmit the data for reception by the relay station.

In one aspect of the invention the remote computing means comprises one of a computer located at a remote base station and a cloud computer server.

Figure 3:
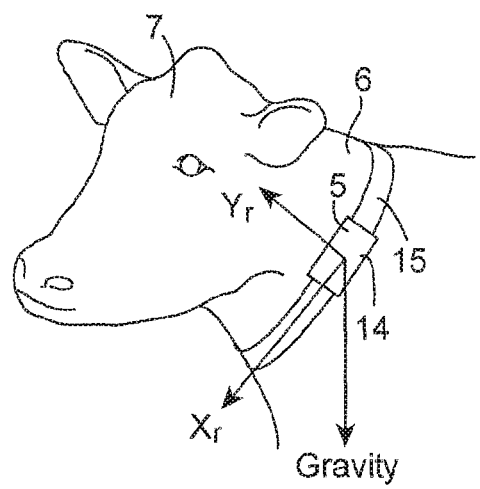
Figure 7:
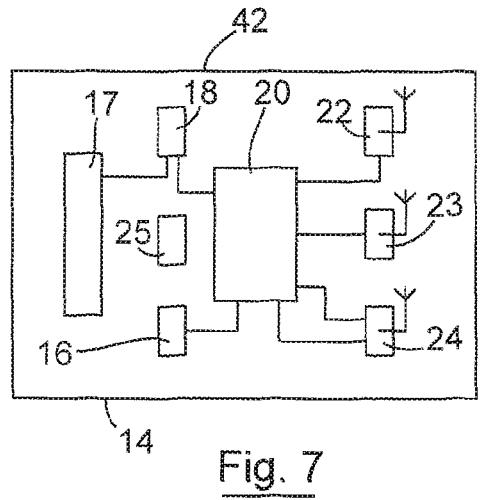
Figure 4:
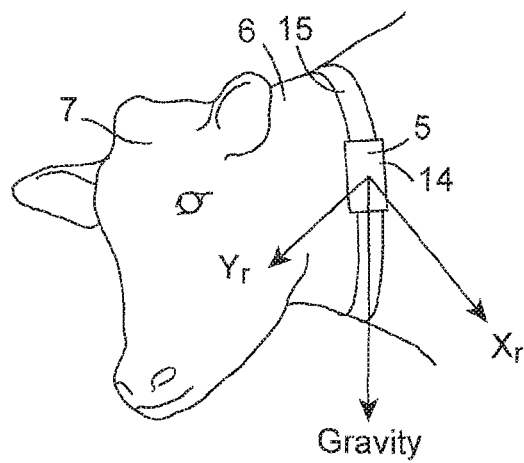
Figure 2:
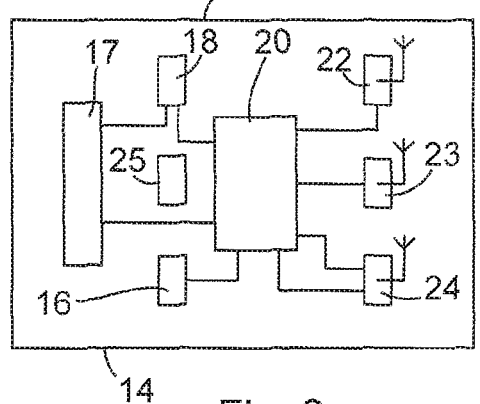
Figure 5:
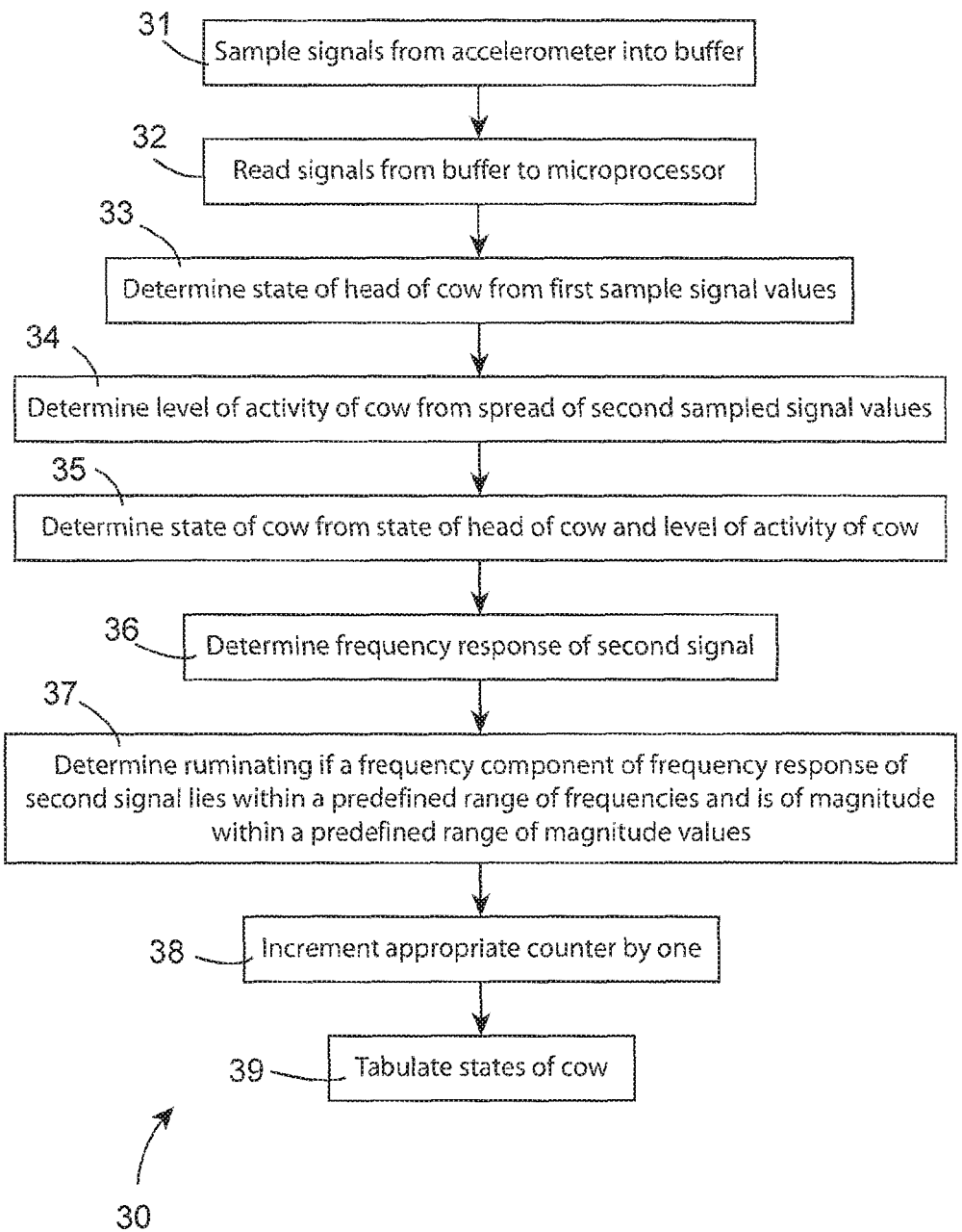
Figure 6:
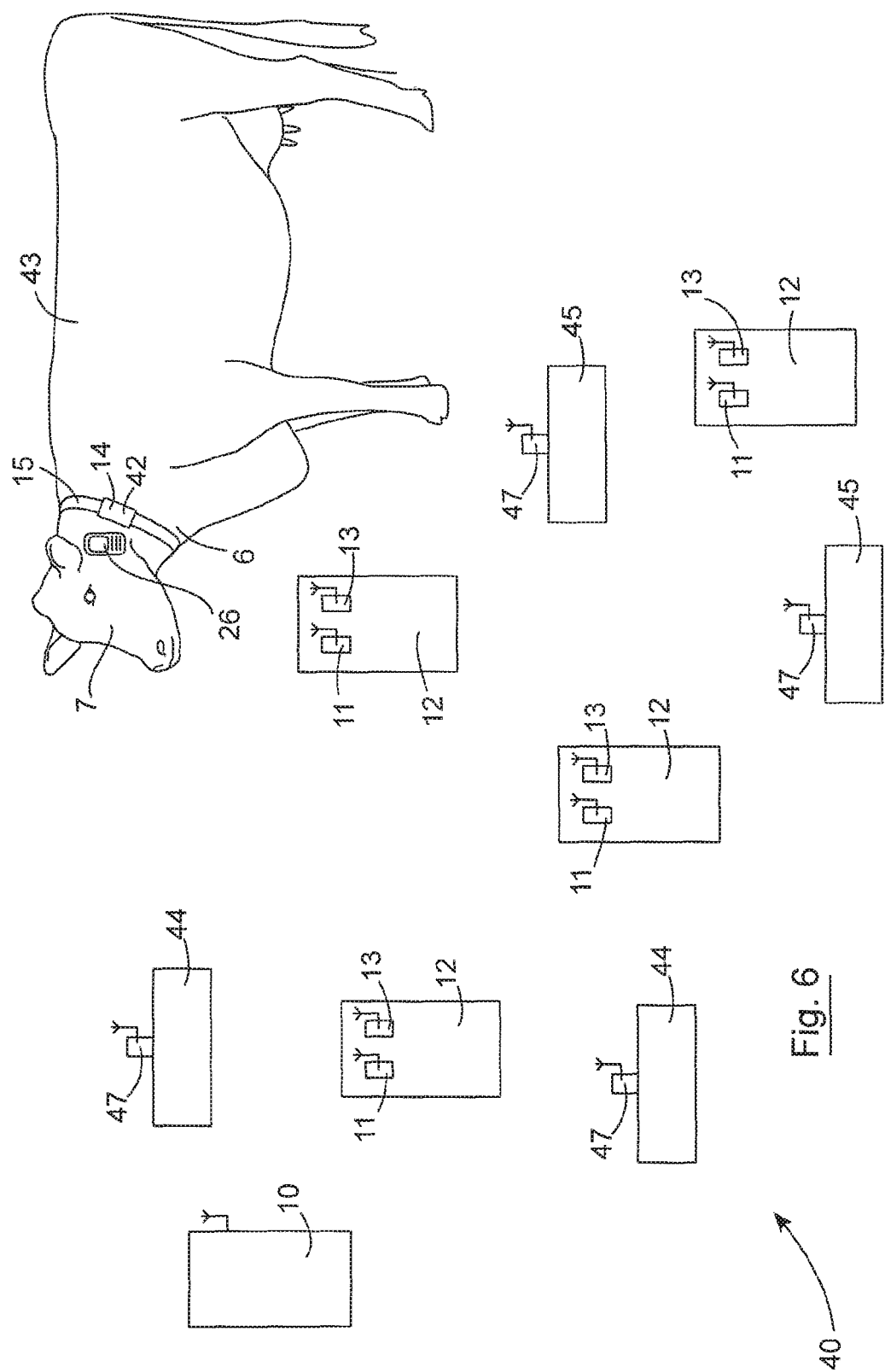

The invention will be more clearly understood from the following description of some preferred embodiments thereof, which are given by way of example only, with reference to the accompanying drawings, in which:

FIG. 1 is a schematic view of a system according to the invention for determining the state of an animal, FIG. 2 is a block representation of a device also according to the invention for determining the state of the animal for use in the system of FIG. 1, FIG. 3 is a side elevational view of a portion of an animal with the device of FIG. 2 attached thereto, FIG. 4 is a side view of a portion of the animal similar to FIG. 3 with the device of FIG. 2 attached to the animal, and with the portion of the animal in a different state to that of FIG. 3, FIG. 5 is a flowchart of a routine carried out by the device of FIG. 1 for determining the state of the animal, FIG. 6 is a schematic view of a system according to another embodiment of the invention for determining the state of an animal, and FIG. 7 is a block representation of a device according to another embodiment of the invention for determining the state of the animal for use in the system of FIG. 6.

Referring to the drawings and initially to FIGS. 1 to 5, there is illustrated a system according to the invention, indicated generally by the reference numeral 1, for determining a state of an animal, in this embodiment of the invention for determining the state of a cow 2 from a plurality of states, including resting, feeding, ruminating and a highly active state. The system 1 comprises a device also according to the invention, indicated generally by the reference numeral 5, for attaching to the animal, namely, for attaching to the neck 6 of the cow 2 for detecting two conditions of the cow 2, namely, a first condition indicative of the state of the head 7 of the cow 2, in other words, whether the head 7 of the cow 2 is in a lowered state corresponding to feeding, or a raised state corresponding, for example, to ruminating and other states of the cow 2 in which the head of the cow 2 would be in a raised state, and a second condition, which in this embodiment of the invention is the level of activity of the cow 2. The state of the cow is determined from the detected state of the head 7 of the cow 2, and from the detected level of activity of the cow 2 as will be described below. However, before describing how the device 5 determines the state of the cow 2, the system 1 and the device 5 will first be described. Typically, each cow 2 of a herd of cows will be provided with one of the devices 5 attached thereto.

The system 1 as well as comprising the device 5 also comprises a remote computing means, which may be a computer located at a remote base station, such as a desktop computer, a laptop computer, a tablet computer or the like. The computer may also comprise a mobile smart phone with computing capacity, or any other suitable computing device. Alternatively, the remote computing means may comprise a cloud computer server. However, in this embodiment of the invention the remote computing means comprises a computer 10 located in a base station.

A plurality of relay stations 12 are provided located strategically around fields, in animal houses, milking parlours and the like for receiving data transmitted by the devices 5 which is indicative of the state of the animal for relaying to the base station 10. Each relay station 12 comprises a short range transceiver 11 for wirelessly transmitting an activation signal, namely, a wake-up signal for reception by the devices 5 as the cows 2, to which the devices 5 are attached, come within range of the relay station 12 to activate the respective devices 5 to transmit data relating to the state of the cow 2. This will be described in more detail below. The transceiver 11 in turn receives the data transmitted by the respective devices 5 in response to the wake-up signal. A long range transmitter 13 is also located in each relay station 12 for transmitting the data relating to the states of the respective cows 2 received from the devices 5 to the base station computer 10.

Turning now to the devices 5, each device 5 comprises a housing 14 which is adapted for securing to the neck 6 of the cow 2 by a strap 15 which extends around the neck 6 of the cow 2. The strap 15 is adapted for securing the housing 5 to the neck 6 of the cow 2 with the housing 14 of the device 5 adjacent one side of the neck 6 as illustrated in FIG. 1. Additionally, the housing 14 is secured to the strap 15 so that the orientation of the housing 14 on the neck 6 of the cow 2 remains substantially constant.

A memory chip 16 located in the housing 14 stores a unique identifying code for identifying the device 5, which in turn, as will be described below, is used for identifying the cow 2.

A sensing means, which in this embodiment of the invention comprises an accelerometer 17 is located within the housing 14 for detecting the state of the head 7 of the cow 2, and also for detecting the level of activity of the cow 2. The level of activity of the cow which is determined is essentially any activity of the cow, for example, motive movement of the cow, movement of any part of the body of the cow, such as, for example, the movement of a limb of the cow, movement of the neck, head and the like of the cow, which is detectable by the accelerometer 17 when it is attached to the cow 2 as will be described below. However, in this embodiment of the invention no distinction between the different types of movement of the cow is made.

The accelerometer 17 is of the type which produces signals which are indicative of the acceleration to which the accelerometer 17 is subjected along three axes which are at right angles to each other, namely, an X-axis, a Y-axis and a Z-axis. In this embodiment of the invention the signals which are indicative of the acceleration to which the accelerometer 17 is subjected along the Z-axis are not used. The accelerometer 17 is located in the housing 14, so that first signals produced by the accelerometer 17, which are indicative of the acceleration to which the accelerometer 17 is subjected along the Y-axis are indicative of the first condition of the cow 2, namely, the state of the head 7, in other words, whether the head 7 of the cow 2 is in the raised state illustrated in FIG. 3 and the lowered state illustrated in FIG. 4, while second signals produced by the accelerometer 17, which are indicative of the acceleration to which the accelerometer 17 is subjected along the X-axis are indicative of the second condition, namely, the level of activity of the animal.

A signal processor, in this embodiment of the invention a microprocessor 20 located in the housing 14 continuously samples the first and second signals from the accelerometer 17 at a sampling rate of 12.5 Hz into a buffer 18 located in the housing 14. At the end of respective consecutive first predefined time periods of 10.24 seconds the microprocessor 20 reads the buffered data from the buffer 18 and determines from the buffered data the state of the cow 2 during each of the respective first predefined time periods. The operation of the microprocessor 20 in determining the states of the cow 2 from the buffered data will be described in detail below.

Communicating means, which in this embodiment of the invention comprises a transceiver 22, a short range receiver 23 and a low energy communications module 24 are located in the housing 14. In this embodiment of the invention the low energy communications module comprises a Near Field Communications module 24, which is described below. The transceiver 22 of each device 5 is adapted for transmitting the data indicative of the state of the cow 2 directly to the base station computer 10, and also to any of the relay stations 12 when the cow 2 to which the corresponding device 5 is attached comes within range of the relay station 12, as will be described below. In this embodiment of the invention the transceiver 22 is operable under the control of the microprocessor 20 in two power modes, namely, a high powered mode for transmitting data directly to the remote base station computer 10, and a low powered mode for transmitting data to one of the relay stations 12 when the cow 2, and in turn the device 5 is within range of the relay station 12. The microprocessor 20 is configured so that on the transceiver 22 receiving a wake-up or activating signal from the base station computer 10, the microprocessor 20 operates the transceiver 22 in the high powered mode and transmits data indicative of the state of the cow 2 stored in the microprocessor 20 directly to the base station computer 10 since the last transmission of data which was made by the device 5. Additionally, the transceiver 22 is operable in the high powered mode for transmitting data indicative of the state of the animal directly to the base station computer 10 in response to the microprocessor 20 determining an emergency arising from the state of the cow 2. The transceiver 22 is operated by the microprocessor 20 in the low powered mode in response to a wake-up or activating signal received by the transceiver 22 from one of the relay stations 12 within which the cow 2 and in turn the device 5 thereof is within the range, for transmitting data relating to the state of the cow 2 since the last data transmission which was made by the device 5, for reception by the transceiver 11 of the relay station 12 to be relayed in turn by the long range transmitter 13 of the relay station 12 to the base station computer 10.

The Near Field Communications module 24 of each device is configured for two-way communications with a portable handheld powered device, for example, a mobile smart phone 26 which is capable of communicating in a Near Field Communications protocol at a frequency in the order of 13.56 MH$_z$. The smart phone 26 is programmed with a software application, namely, an app in order to facilitate two-way communications in the Near Field Communications protocol with the device 5 through the Near Field Communications module 24. The communication range of the Near Field Communications module 24 is approximately 40 mm to 50 mm. The microprocessor 20 and the Near Field Communications module 24 are configured to facilitate programming and reprogramming of the microprocessor 20 through the Near Field Communications module 24 by the smart phone 26 operating under the control of the app.

Additionally, the microprocessor 20 and the Near Field Communications module 24 are configured so that the identifying code stored in the memory chip 16 of the device 5 can be read out of the memory chip 16 into the smart phone 26 to facilitate cross-referencing of the identifying code of the device 5 with the identity of the cow 2 to which the device is attached, so that each device 5 is identified with the cow 2 to which that device is attached. The identifying code of each device 5 is cross-referenced with the identity of the corresponding cow 2 in the smart phone 26, and also in the base station computer 10.

Additionally, the smart phone 26 may store the identifying code of each device cross-referenced with the identity of the corresponding cow, and any other data relating to that cow 2 in the smart phone 26 under the control of the app, and may also store the identifying code of the device 5 cross-referenced with the identity of the cow 2 and any other data relating to the cow 2 which may be stored in a cloud database. The Near Field Communications module 24 is also configured so that data may be downloaded from and uploaded to each device 5 by the smart phone 26 under the control of the app. The downloaded data would be any data stored in the devices 5 by the corresponding microprocessors 20, including but not limited to data indicative of the states of the respective cows stored by the corresponding microprocessor 20. Such data would be read from or written to the device 5 by the smart phone 26 in a Near Field Communications protocol under the control the smart phone 26.

The receiver 23 of each device 5 comprises an inductively coupled low frequency signal receiver coil which typically operates at 120 to 140 kHz. The receiver 23 is provided for receiving identification signals from predefined locations visited by the cow 2 to which the device 5 is attached. The microprocessor 20 on reading an identification signal of a predefined location received by the receiver 23 records the identity of the predefined location from the received identification signal, the time at which the identification signal is received and the duration of reception of the identification signal. The identity of the predefined locations, the times of the visits to the predefined locations by the cow 2 and the durations of the visits are stored in the microprocessor 20 for subsequent transmission through the transceiver 22 or the Near Field Communications module 24. Transmitters, which are described with reference to the device which is described with reference to FIGS. 6 and 7, which transmit such identification signals typically are located adjacent water troughs, feeding troughs and the like, so that when such water troughs and feeding troughs are visited by the cow 2 to which the device 5 is attached, a record of the visits, the times and the durations of the visits to such troughs are recorded and stored by the microprocessor 20. This aspect of the device 1 is not further described in respect of the device 5, but is described in detail with respect to the device which is described with reference to FIGS. 6 and 7.

A battery 25 located in the housing 14 powers the components of the device 5 requiring electrical powering.

The operation of the microprocessor 20 in determining the state of the cow 2 will now be described with reference to FIG. 5, which illustrates a flowchart 30 of a software routine through which the microprocessor 20 is programmed to operate. Under block 31 of the flowchart 30, the microprocessor 20 samples the first and second signals read from the accelerometer 17 which are indicative of the acceleration to which the accelerometer 17 is subjected along the X and Y axes, respectively, into the buffer 18 at the sampling rate of 12.5 Hz during each first predefined time period of 10.24 seconds. In block 32 at the end of each first predefined time period, the sampled values of the first and second signals are read by the microprocessor 20 from the buffer 18. In block 33 the microprocessor 20 determines the average value of the sampled values of the first signal. If the average value of the sampled values of the first signal is below a predefined threshold value, the microprocessor 20 determines the head 7 of the cow 2 to which the device 5 is attached to be in the lowered state. On the other hand, if the average value of the sampled values of the first signal is above the predefined threshold value, the microprocessor 20 determines that the head 7 of the cow 2 is in the raised state. However, it will be appreciated that in some configurations of the accelerometer, the average value of the sampled values of the first signal being above the predefined threshold value may be indicative of the head of the cow 2 being in the lowered state, and an average value of the sampled values being below the predefined threshold value may be indicative of the head of the cow 2 being in the raised state.

In block 34 the microprocessor 20 determines the spread of the sampled values of the second signal in order to determine the level of activity of the animal. In this embodiment of the invention the microprocessor 20 is programmed to measure the standard deviation of the sampled values of the second signal. Having computed the standard deviation of the second signal, the microprocessor 20 proceeds to block 35, which compares the standard deviation of the second signal with first, second, third and fourth predefined ranges of standard deviation. The first predefined range of standard deviations is indicative of the animal feeding, and is greater than the second predefined range of standard deviations which is indicative of the animal being in a resting state. The third predefined range of standard deviations may be indicative of the animal ruminating, and lies between the first and second predefined ranges of standard deviation. The fourth predefined range of standard deviations is indicative of a highly active state of the animal, and is greater than the first predefined range of standard deviations.

Irrespective of the determined state of the head 7 of the cow 2, if the standard deviation of the sampled values of the second signal is within the second predefined range of standard deviations, the microprocessor 20 determines that the cow 2 is resting, and the microprocessor 20 moves to block 38, which is described below. If the microprocessor 20 determines that the first signal is indicative of the head of the animal being in the lowered state and the standard deviation of the sampled values of the second signal lies within the first predefined range of standard deviations, the microprocessor 20 determines the state of the animal as being feeding, and the microprocessor 20 moves to block 38. If the sampled values of the first signal are indicative of the head 7 of the cow 2 being in the raised state, and the standard deviation of the sampled values of the second signal lie within the third predefined range of standard deviation values which is indicative of the possibility of the cow 2 ruminating, the microprocessor 20 moves to block 36, which analyses the frequency domain of the second signal.

In this embodiment of the invention a Fast Fourier Transform is carried out on the sampled values of the second signal by the microprocessor 20 for that first predefined time period in order to produce the frequency response of the second signal. The microprocessor 20 then moves to block 37 and determines if a frequency component or components of the frequency response of the second signal lie within a predefined frequency range which is indicative of ruminating, and if so, the magnitude of that frequency component or the magnitudes of those frequency components which are within the predefined frequency range are determined. If only one frequency component of the frequency response of the second signal lies within the predefined frequency range, and the magnitude of that frequency lies within a predefined range of magnitude values, then the microprocessor 20 determines that the animal is ruminating. If, on the other hand, two or more of the frequency components of the frequency response of the second signal lie within the predefined frequency range, the average value of the magnitude of those frequency components which lie within the predefined frequency range is computed, and if the computed average magnitude value lies within the predefined range of magnitude values, the microprocessor 20 determines that the animal is ruminating. It is known that the frequency of ruminating by an animal lies in the range of 0.7 Hz to 1.4 Hz. Depending on how the accelerometer 17 detects the frequency of ruminating, the predefined range of frequencies within which one or more of the frequency components of the frequency response of the second signal must lie may correspond directly with the frequency of rumination, namely, between 0.7 Hz and 1.4 Hz, or a frequency range which is indicative of the ruminating frequency range of 0.7 Hz to 1.4 Hz. If in block 37 the microprocessor 20 determines that the cow 2 is ruminating, the microprocessor 20 moves to block 38.

If the microprocessor 20 determines from the sampled values of the first signal that the head of the animal is in the raised state and the standard deviation of the sampled values of the second signal lie within the fourth predetermined range of standard deviation values which is indicative of a highly active state of the cow 2, the microprocessor 20 determines that the cow 2 is in a highly active state, and the microprocessor moves to block 38.

The microprocessor 20 is configured with four counters corresponding to the four states of the cow 2. In block 38 at the end of each first predefined time period, the counter corresponding to the determined state of the cow for that first predefined time period is incremented by one by the microprocessor 20.

In block 39 at the end of each of respective consecutive second predefined time periods, which in this embodiment of the invention is 15 minutes, the microprocessor 20 tabulates from the four counters the number of the first predefined time periods the cow 2 was in each of the respective states during that second predefined time period, and this data is stored by the microprocessor 20 for each second predefined time period for subsequent transmission. Additionally, at the end of each second predefined time period, the four counters are reset to zero.

Turning now to the recovery of data from the devices 5. In normal operation of the devices 5, no data is transmitted until the cow 2 to which one of the devices 5 is attached comes within range of one of the relay stations 12. On receiving a wake-up signal from the short range transceiver 11 of the relay station 12 through the transceiver 22 of the device 5 now within range of the transceiver 11 of the relay station 12, the microprocessor 20 of that device 5 operates the transceiver 22 in the low powered mode, and transmits through the transceiver 22 the stored data relating to states of the cow 2 during each one of the second predefined time periods of 15 minutes, and the number of the first predefined time periods that the cow 2 was in each of those states for each of the second predefined time periods since the last transmission of data from that device 5 occurred. The stored data, which has been stored in the microprocessor 20 since the last transmission of data, relating to the identity of the predefined location visited by the cow 2, the times of the visits and the durations of the respective visits is also transmitted through the transceiver 22 along with the stored data relating to the states of the cow 2. The transmitted data is received by the short range transceiver 11 of the relay station 12, which in turn relays the data to the base station computer 10 through the long range transmitter 13.

The data is packaged for transmission by the microprocessor 20 into data packets, with the data packet comprising the identifying code of the device 5 stored in the memory chip 16 along with the data relating to the states of the cow 2 during the respective second predefined time periods and the number of the first predefined time periods that the cow 2 was in each of those states during each of the respective second predefined time periods, as well as the data relating to the identity of the predefined locations visited by the cow 2, the times of the visits and the durations of the visits.

In the event that a period greater than a predefined time period has elapsed since the last transmission from one of the devices 5 has been received by the base station computer 10, the base station computer 10 transmits an activation signal for reception by the transceiver 22 of that device 5 to activate the microprocessor 20 of that device 5 to transmit the data indicative of the states of the animal since the last transmission from that device was made. On receipt of the activation signal, the microprocessor 20 operates the transceiver 22 in the high powered mode, and transmits through the transceiver 22 the stored data relating to the states of the cow 2 during each one of the second predefined time periods and the number of the first predefined time periods the cow 2 was in each of those states for each of the second predefined time periods since the last transmission of data from that device 5 was made for direct reception by the base station computer 10.

By operating the transceiver 22 of the device 5 in the low powered mode for transmissions of data to the relay stations 12, significant power saving is achieved in the device 5. Accordingly, provided that the interval between transmissions of data indicative of the states of the cow made by each device 5 to the relay stations 12, and in turn to the base station computer 10 are less than the predefined time interval, the transmissions of the data indicative of the states of the cow 2 are made with the transceiver 22 of the corresponding device 5 operating in the low powered mode.

In the event that the microprocessor 20 determines that during a number of consecutive second predefined time periods the state of the animal has remained in a highly active state, which could be indicative of the onset of oestrus, the microprocessor 20 is programmed to operate the transceiver 22 in the high powered mode and to output an alert signal through the transceiver 22 for reception by the base station computer 10. The alert signal includes the identifying code of the device 5 together with a signal alerting to the continuous highly active state of the animal.

The base station computer 10 is programmed to carry out further processing of the received data for determining various health states of the animal as will be described briefly below. The base station computer 10 is programmed to determine various health states of the respective cows 2 from the data received from the respective devices 5 attached to the cows. For example, the onset of oestrus, is determined by comparing the highly active state of the cow 2 to historical states of the cow 2 and to the active states of other cows in the same herd. In the event of the highly active state in the cow 2 being greater than its normal active state and being greater than the highly active state of the other cows in the herd, then the onset of oestrus would be indicated, as would other reproductive issues, for example, cystic ovarian diseases be indicated. Lameness would be indicated in the case of an animal resting excessively. Lack of ruminating and feeding of the animal would be indicative of an animal as being in poor health.

In use, each cow 2 of a herd of cows will be provided with one of the devices 5 attached to the neck 6 of the corresponding cow 2 by the corresponding strap 15 as already described. Initially the identifying code of the respective devices 5 are sequentially read from the devices 5 through the Near Field Communications module 24 by the smart phone 26 which is programmed with the appropriate app. The identifying codes of the respective devices 5 are stored and cross-referenced in the smart phone 26 with the actual identity of the corresponding cows 2. This cross-referenced stored data is relayed to the base station computer 10 by the smart phone 26 and stored also in the base station computer 10 so that the base station computer 10 can readily identify the animals from the corresponding identifying codes of the respective devices 5.

If any programming or reprogramming of the microprocessors 20 in the respective devices 5 is required, the necessary programming or reprogramming is carried out by the smart phone 26 operating under the control of the app through the Near Field Communications module 24 of the relevant device 5.

As each cow 2 comes within range of the short range transceiver 11 of any one of the relay stations 12, the device 5 is activated in response to a wake-up signal received from the short range transceiver 11, and the device 5 transmits through the transceiver 22 operating in the low powered mode the data relating to the states of the cow 2 during the second predefined time periods since the last transmission from that device 5 was made. The data relating to the state of the cow 2 received by the relay station 12 is then transmitted by the long range transmitter 13 of the relay station 12 to the base station computer 10. The base station computer 10 then carries out further analysis of the received data to determine the health and other states of the cow 2 from the received data.

If the microprocessor 20 of any of the devices 5 determines that the corresponding cow 2 remains in a highly active state during a predefined number of second predefined time periods which could be indicative of oestrus, the transceiver 22 is operated in the high powered mode, and an alert signal is transmitted directly to the base station computer 10 by the transceiver 22 of that device 5. The alert signal includes the identifying code of the device 5 and data relating to the highly active state of the cow over the relevant predefined number of second predefined time periods.

Where it is desired to download data relating to the states of the cow onto the smart phone 26, the smart phone 26 is operated under the control of the app and is brought into close proximity within 50 mm of the device 5 from which the data is to be downloaded. An activation signal is produced by the smart phone 26 and is transmitted in a Near Field Communications protocol for reception by the Near Field Communications module 24 of the device 5. On receipt of the activation signal, the microprocessor 20 is operated to download the data in a Near Field Communications protocol through the Near Field Communications module 24 to the smart phone 26. The data relating to the states of the animal is packaged in data packets which include the identity code of the device 5 and the data relating to the states of the cow 2 as already described.

Referring now to FIGS. 6 and 7, there is illustrated a system according to another embodiment of the invention, indicated generally by the reference numeral 40, which comprises a device 42 also according to the invention and indicated generally by the reference numeral 42. The system 40 and the device 42 are provided for determining the state of an animal, in this case a cow 43, and are substantially similar to the system 1 and the device 5, respectively, described with reference to FIGS. 1 to 5, and similar components are identified by the same reference numerals. However, in this embodiment of the invention the system 40 and the device 42 as well as determining the states of the cow 43, also stores data indicative of the identity of predefined locations visited by the cow 43, for example, drinking troughs 44, feeding troughs 45 and other such locations. In this embodiment of the invention each predefined location 44, 45 is provided with a short range transmitter 47 for wirelessly and intermittently, typically at one-second intervals, transmitting an identification signal containing data identifying the corresponding predefined location 44, 45 for reception by the receiver 23 of the device 42. In this embodiment of the invention each transmitter 47 has a transmission range for transmitting the corresponding identification signal of not more than a few metres, depending on the size and length of the drinking trough or feeding trough, so that the identification signal is only picked up by the short range transceiver 23 of the device 5. The identification signal is a low frequency signal of frequency typically in the range of 120 kHz to 140 kHz for reception by the inductively coupled receiver 23.

The signal processor 20 is configured to read the identification signals received from the predefined locations 44, 45 and to store the data indicative of the identity of each predefined location 44, 45 visited by the cow 43, as well as the times at which the animal visited the predefined locations 44, 45 and the duration of each of the visits of the cow 43 to the predefined locations 44, 45. This data regarding the identity of the predefined locations, the times at which the predefined location 44, 45 are visited and the durations of the visits during each second predefined time period is stored by the microprocessor 20 for each of the second predefined time periods, and is transmitted with the data relating to the states of the cow 43 during the second predefined time periods when the data stored for the respective predefined second time periods is being transmitted to the base station computer 10 or to one of the relay stations 12 for relaying to the base station computer 10. On receipt of the data indicative of the predefined locations 44, 45 visited by the cow 43, the times and durations of the visits, the base station computer 10 by analysing the data can determine if the cow 43 is drinking sufficiently and feeding sufficiently, and from this data the health of the cow 43 can also be determined.

In this embodiment of the invention the data relating to the states of the animal and the predefined locations visited by the animal together with the times and durations of the visits may also be downloaded through the Near Field Communications module 24 to the smart phone 26 operating under the control of the app.

While the devices 5 and 42 have been described as comprising a sensing means provided by an accelerometer, any other suitable sensing means could be provided. For example, it is envisaged that a tilt switch could be provided for determining the state of the head of the animal, and other suitable movement and activity detectors could be provided for detecting the level of activity of the animal.

Additionally, it will be appreciated that while the devices according to the invention have been described as comprising a microprocessor for processing the signals read from the accelerometer or other sensing means, in certain cases, it is envisaged that the microprocessor may be dispensed with, and the processing of the signals produced by the sensing means would be carried out remotely, for example, in a base station computer, a mobile smart phone or the like, or in a cloud computer server. In which case, it is envisaged that the raw data produced by the sensing means would be transmitted unprocessed by the devices to the base station computer, mobile smart phone or other such remote device.

It will also be appreciated that while the devices have been described as being secured to the side of the neck of an animal, the devices may be secured in any suitable position on the neck or head or other suitable part of the animal, or the devices may be implanted in the animals.

It will also be appreciated that while the systems have been described as comprising a plurality of relay stations, in certain cases, the relay stations may be omitted, and the devices would be configured to communicate directly with the base station computer or a smart phone.

While it is desirable, it is not essential that the devices should comprise a Near Field Communications module, and the receiver 23 could also be dispensed with if a record of predefined locations visited by the animal is not required.

It will also be appreciated that while the devices, method and systems have been described for determining specific states of a cow, the devices, method and systems may be provided for determining other states of a cow or indeed any states of any other animal.

It is also envisaged that data relating to the state or states of the cow may be read from the devices 5 and 42 by the smart phone 26 through the Near Field Communications module 24 of the devices in a Near Field Communications protocol.

While the signals indicative of the acceleration to which the accelerometer is subjected along the X and Y axes only have been used in determining the states of the animal, it is envisaged that the signals indicative of the acceleration to which the accelerometer is subjected along the three axes at right angles to each other, namely, the X, Y and Z axes, may be used in determining the state of the animal. It is envisaged that an animal lying on its side could be detected from signals indicative of the acceleration to which the accelerometer is subjected along the Z-axis. It is also envisaged that a more accurate indication of the activity of the animal could be determined by using the signals from the accelerometer indicative of the acceleration to which the accelerometer is subjected along both the X and the Z axes. In particular, it is possible that by using the signals indicative of the acceleration to which the accelerometer is subjected along the X and Z axes, it may be possible to differentiate between motive movement of the animal, and other movement of the animal, such as movement of the neck of the animal or other parts thereof.

It is also envisaged that by reading signals from the accelerometer indicative of the acceleration to which the accelerometer is subjected along the Z-axis, if the devices are secured to the animal with the Z-axis appropriately located, the signals read from the accelerometer indicative of the acceleration to which the accelerometer is subjected along the Z-axis would be indicative of an animal lying on its side if the animal were lying on its side. This data could also be subsequently analysed by the base station computer, and if the animal were detected to be lying on its side for extended periods, this could be an indication of ill health of the animal.

While the devices have been described for detecting the states of a cow, it will be readily apparent to those skilled in the art that the devices may be used for detecting the states of any other animal besides a cow.

It is also envisaged that the devices may be secured to the animals by other means besides a strap, for example, in certain cases, it is envisaged that the devices may be implanted in the animals at appropriate locations, and when implanted would be located relatively closely to the skin of the animal in order to facilitate Near Field Communications with the devices.

While the system 40 and the device 42 have been described as receiving transmitted identification signals of the respective predefined locations on visiting of such predefined locations by an animal, it is envisaged that instead of transmitters for transmitting identification signals being provided at each predefined location, an RFID device may be provided at each predefined location, which on transmission of a signal by the short range transceiver 23 of the device 5 would reflect and alter the transmitted signal so that the reflected signal would include the identification of the corresponding predefined location.

Additionally, it is envisaged that in order to save power, the devices 5 and 42 may be operated to minimise the number of transmissions of data from the devices 5 and 42 to the relay stations. This would be carried out by preventing transmissions to the relay stations unless a predefined elapsed time had passed since the last transmission had been made by the device 5 or the device 42.

The invention claimed is:

1. A method for determining a state of an animal, the method comprising:
    providing a sensing means for sensing two conditions of the animal, a first one of the sensed conditions comprising an orientation of a head of the animal, and a second one of the sensed conditions comprising a level of activity of the animal, the sensing means comprising an accelerometer configured to produce signals indicative of acceleration to which the accelerometer is subjected along two axes perpendicular to each other,
    attaching the accelerometer to the animal to produce signals indicative of the first and second sensed conditions,
    providing a signal processor configured to read the signals from the accelerometer indicative of the first and second sensed conditions,
    operating the signal processor
    to read the signals from the accelerometer indicative of the first and second sensed conditions of the animal,
    to determine at least one state of the animal from a plurality of states as being ruminating in response to
    the read signals indicative of the first one of the sensed conditions being indicative of the head of the animal being in a raised state,
    two or more frequency components of the read signals indicative of the second one of the sensed conditions lying within a predefined frequency range indicative of ruminating, and
    an average value of magnitude values of the frequency components of the read signals of the second one of the sensed conditions lying within the predefined frequency range indicative of ruminating being within a predefined range of magnitude values indicative of ruminating.

2. A method as claimed in claim 1 in which one of the determined states of the animal is feeding, and the state of the animal is determined as feeding in response to the read signal indicative of the first one of the sensed conditions being indicative of the head of the animal being in a lowered state, and the second one of the sensed conditions indicative of the level of activity of the animal being indicative of a low level of activity indicative of feeding.

3. A device for determining the state of an animal, the device comprising a sensing means for monitoring two conditions of the animal and for producing signals indicative of the sensed conditions, the sensing means comprising an accelerometer configured to produce signals indicative of acceleration to which the accelerometer is subjected along two axes perpendicular to each other, the accelerometer being configured for attaching to the animal to produce the signals indicative of the sensed conditions, and a signal processor configured to read the signals from the accelerometer, and to carry out the method as claimed in claim 1 for determining the state of the animal.

4. A system for determining a state of an animal, the system comprising a device as claimed in claim 3 for determining the state of an animal, and a remote computing means for receiving data communicated wirelessly by the device.

5. A method as claimed in claim 2 in which the read signal indicative of the second one of the sensed conditions is determined as being indicative of a low level of activity of the animal which is indicative of feeding in response to a spread of values of the magnitude of the read signals indicative of the second one of the sensed conditions lying within a first predefined range of magnitude values indicative of feeding.

6. A method as claimed in claim 5 in which one of the determined states of the animal comprises resting, and the state of the animal is determined as resting in response to the read signal indicative of the second one of the sensed conditions being indicative of a low level of activity of the animal indicative of resting.

7. A method as claimed in claim 5 in which the state of the animal is determined as being in a highly active state in response to the read signals indicative of the first one of the sensed conditions being indicative of the head of the animal being in a raised state, and the second one of the sensed conditions being indicative of a high level of activity of the animal.

8. A method as claimed in claim 5 in which the read signal indicative of the second one of the sensed conditions is determined as being indicative of a low level of activity which is indicative of feeding in response to the spread of the values of the magnitude of the read signal indicative of the second one of the sensed conditions about a mean value thereof lying within a range indicative of the first predefined range of magnitude values.

9. A method as claimed in claim 6 in which the read signals indicative of the second one of the sensed conditions is determined as being indicative of a low level of activity which is indicative of resting in response to a spread of values of the magnitude of the read signal indicative of the second one of the sensed conditions lying within a second predefined range of magnitude values indicative of resting.

10. A method as claimed in claim 9 in which the second predefined range of magnitude values of the spread of values of the magnitude of the read signal indicative of the second one of the sensed conditions is less than the first predefined range of magnitude values of the spread of values of the magnitude of the read signal indicative of the second one of the sensed conditions.

11. A method as claimed in claim 9 in which the read signals indicative of the second one of the sensed conditions is determined as being indicative of a low level of activity of the animal which is indicative of resting in response to the spread of the values of the magnitude of the read signal indicative of the second one of the sensed conditions about a mean value thereof lying within a range indicative of the second predefined range of magnitude values.

12. A method as claimed in claim 9 in which the state of the animal is determined as ruminating in response to the spread of values of the magnitude of the read signal indicative of the second one of the sensed conditions lying within a third predefined range of magnitude values indicative of ruminating.

13. A method as claimed in claim 12 in which the third predefined range of magnitude values lies between the first predefined range of magnitude values and the second predefined range of magnitude values.

14. A method as claimed in claim 12 in which the state of the animal is determined as ruminating in response to the spread of the values of the magnitude of the read signal indicative of the second one of the sensed conditions about a mean value thereof lying within a range of magnitude values indicative of the third predefined range of magnitude values.

15. A method as claimed in claim 7 in which the state of the animal is determined as being in a highly active state in response to a spread of values of the magnitude of the read signal indicative of the second one of the sensed conditions lying within a fourth predefined range of magnitude values indicative of the highly active state.

16. A method as claimed in claim 15 in which the fourth predefined range of magnitude values is greater than the first predefined range of magnitude values.

17. A method as claimed in claim 15 in which the animal is determined as being in the highly active state in response to the spread of the values of the magnitude of the read signal indicative of the second one of the sensed conditions about a mean value thereof lying within a range indicative of the fourth predefined range of magnitude values.

18. A method as claimed in claim 1 in which the orientation of the head of the animal and a spread of the values of the magnitude of the read signal indicative of the second one of the sensed conditions are initially determined.

19. A method as claimed in claim 12 in which the frequency of the read signal is analysed in order to determine if the animal is ruminating, in response to the head of the animal being determined as being in the raised state, and the spread of values of the magnitude of the read signal indicative of the second one of the sensed conditions lying within the third predefined range of magnitude values.

* * * * *